United States Patent [19]

MacBride et al.

[11] Patent Number: 4,577,110

[45] Date of Patent: Mar. 18, 1986

[54] OPTICAL APPARATUS AND METHOD FOR MEASURING THE CHARACTERISTICS OF MATERIALS BY THEIR FLUORESCENCE

[75] Inventors: William R. MacBride, Glenmore; James A. Magee, Exton; William B. Armiger, King of Prussia; Dane W. Zabriskie, West Chester, all of Pa.

[73] Assignee: BioChem Sensors, Inc., Malvern, Pa.

[21] Appl. No.: 483,559

[22] Filed: Apr. 11, 1983

[51] Int. Cl.⁴ .................. G01J 3/443; G01N 21/64
[52] U.S. Cl. .................. 250/461.2; 356/317; 356/417
[58] Field of Search ............... 356/311, 317, 318, 417; 250/461.1, 461.2, 458.1, 365

[56] References Cited

U.S. PATENT DOCUMENTS

| | | | |
|---|---|---|---|
| 2,971,429 | 2/1961 | Howerton | 356/308 |
| 3,068,739 | 12/1962 | Hicks, Jr. et al. | 356/41 |
| 3,510,648 | 5/1970 | Leger, Jr. | 250/364 |
| 3,854,050 | 12/1974 | Peterson et al. | 250/328 |
| 3,918,812 | 11/1975 | Holm | 250/459.1 |
| 3,941,477 | 3/1976 | Schodl | 356/342 |
| 4,031,399 | 6/1977 | Klein et al. | 250/461.2 |
| 4,055,768 | 10/1977 | Bromberg | 356/317 |
| 4,153,675 | 5/1979 | Kleinerman | 250/458.1 |
| 4,293,225 | 10/1981 | Wheaton et al. | 250/461.1 |
| 4,295,199 | 10/1981 | Curry et al. | 250/461.2 |
| 4,447,546 | 5/1984 | Hirschfeld | 356/417 |

FOREIGN PATENT DOCUMENTS

| | | | |
|---|---|---|---|
| 0197451 | 12/1982 | Japan | 250/458.1 |
| 2078941 | 1/1982 | United Kingdom . | |

OTHER PUBLICATIONS

*European J. Appl. Microbiol. Biotechnol.*, V. 13, pp. 10–14, 1981.
Anal. Chem., V. 48, N. 14, pp. 2275–2278, 12/76.
*Photoluminescence of Solutions, with Applications to Photochemistry and Analytical Chemistry*, C. A. Parker, 1968, pp. 226–229.
*Appl. Environ. Microbiol.*, V. 35, No. 2, pp. 337–343.
*Science*, vol. 217, 8/6/82, pp. 537–540.
*Appl. Microbiol.*, vol. 19, 1970, pp. 446–450.
"Application of Laser Technology to Atmospheric Monitoring," A. Mooradian, Nat. Bureau of Standards Special Publ. 464, 9/20/76, p. 277.
"Stroboscopic Time-Resolved Spectroscopy," Bhaumik et al., *The Review of Scientific Instruments*, vol. 36, No. 1, Jan. 1965, p. 37.
"Phosphorimetry: A New Method of Analysis," Keirs et al., *Analytical Chemistry*, vol. 29, No. 2, Feb. 1957, p. 203.

Primary Examiner—F. L. Evans
Assistant Examiner—Joel L. Harringa
Attorney, Agent, or Firm—Austin R. Miller

[57] ABSTRACT

An improved apparatus and method for monitoring the characteristics of materials by their fluorescence are described. A unique design is employed in which common fields of view are provided for the optical paths for the illuminating light and the emitted fluorescence. In a preferred form they are coaxial. This permits the apparatus to be contained within a probe which may be inserted directly in a vessel containing the material to be analyzed. The device is specifically designed to withstand sterilization with steam, to operate aseptically within biological processes, and to maintain a high stability and sensitivity over extended periods of time.

2 Claims, 11 Drawing Figures

OPTICAL APPARATUS AND METHOD FOR MEASURING THE CHARACTERISTICS OF MATERIALS BY THEIR FLUORESCENCE

FIELD OF THE INVENTION

This invention relates to an improved apparatus and method for monitoring the characteristics of materials by their fluorescence.

BACKGROUND OF THE INVENTION

The prior art has employed various devices to measure the fluorescence of materials. Fluorometers illuminate materials with selected wavelengths of light and measure the fluorescence emitted at specific wavelengths which are longer than those used to illuminate the material. Conventional laboratory spectrofluorometers employ rectangular quartz sample chambers wherein the excitation source illuminates the sample through one side of the chamber and the emitted fluorescence is measured through another side of the chamber. The emitted light may be measured through the window at 90° or 180° with respect to the window used to illuminate the sample. Instruments of this design are generally used to analyze discreet samples off-line with respect to the process. Flow-through chambers are also available for a limited number of on-line applications.

Instruments with sample chambers are unsuited for most on-line applications. There are many practical difficulties with supplying samples to flow cells which are representative of the contents of a larger vessel. In highly light-absorbant samples, only the layer of sample immediately adjacent to the window through which the illuminating light passes will fluoresce. The emitted light cannot reach the window on which the detector is focused. In dilute samples where only a portion of the illuminated light is absorbed by the sample, greater sensitivity could be achieved if the sample chamber were enlarged so that more fluorophores were present in the field of view for the detector. This suggests that sample chamber sizes should vary with sample characteristics to maximize sensitivity. Alternatively, samples could be diluted to a specific fluorescence value. Both procedures are obviously impractical for on-line applications. In many cases, however, these instruments are not suitable for on-line applications because of poor sensitivity to highly light-absorbent samples and difficulties in supplying samples to a flow cell which are representative of the contents of a larger reactor.

Other fluorometer designs employ surface detectors which use a single transparent window to illuminate the material and observe the emitted fluorescence. The surface detector principle is reported to have greater sensitivity with highly light-absorbent samples than instruments that use the rectangular sample chamber. (Photoluminescence of Solutions, With Applications to Photochemistry and Analytical Chemistry, C. A. Parker, 1968, pp. 226-229). The surface detector principle also permits improved on-line process capabilities. For example, one instrument has been described which was attached to the side of a glass fermentor to obtain on-line fluorescence measurements of the culture within the fermentor. (Fluorimetric Technique for Monitoring Changes in the Level of Reduced Nicotinamide Nucleotides in Continuous Cultures of Microorganisms, D. E. F. Harrison and Britton Chance, 1969, pp. 446-450). This design used a lamp source and detector aimed at a common spot on the surface of the window adjacent to the sample and at 60° to one another. The practical limitations to this design are many. The application is dependent on a transparent vessel or one equipped with a window. With a fixed angle between them, this requires that the distance between the sample interface and the instrument be fixed at an optimal value. Since this distance is partly a function of the vessel window assembly, the instrument must be custom designed to each vessel type. Mixing is poor at any vessel surface so that the material nearest the fluorometer may not be representative of the vessel contents. The long term stability of this instrument was low. (Applied and Environmental Microbiology, Estimation of Fermentation Biomass Concentration by Measuring Culture Fluorescence, D. W. Zabriskie and A. E. Humphrey, 1978, pp. 337-343). It also makes inefficient use of the illuminating light at low concentrations of fluorophore. In this case, the excitation light may penetrate several feet into the tank. Since the detector is looking in a direction 60° from the path of illumination, the amount of observable fluorescence is low.

A probe is described which uses a complicated system of lenses to collimate the illuminating light and emitted fluorescence, and a dichroic mirror to separate the paths of the illuminating lights and emitted fluorescence to form an angle of 90° with respect to one another. (European Journal of Applied Microbiology and Biotechnology, On-Line Measurements of Culture Fluorescence: Method and Application, W. Beyeler, A. Einsele, and A. Fiechter, pp. 10-14, 1981). This system makes poor use of light since the dichroic mirror is a relatively inefficient device and light losses through refraction are large owing to the number of surfaces associated with the lenses, filters, and dichroic mirror. These factors made it necessary to cool the probe using an external source of cooling water in order to increase instrument sensitivity since the detector performance is inversely related to temperature. A practical lower temperature limit of 15° C. was realized however, since lower temperatures lead to water condensation from the atmosphere inside the probe. This probe is not well suited to industrial use. The need to separate the paths for the illuminating light and emitted fluorescence resulted in an unsymmetrical and bulky configuration difficult to seal from the operating environment. The lenses and their proper alignment are fragile. The lenses must be fabricated from non-fluorescent materials and are expensive, especially when manufactured from quartz for UV applications. Since the performance of the dichroic mirror and lens system must be optimized for a specific combination of illuminating light and emitted fluorescence wavelengths, probe modifications are required when it is desired to change the wavelength combination. Moreover, because of the inherent fixed refraction characteristics of the lenses, and because the illuminating light has a different wavelength from that of the emitted fluorescence, the apparatus provides a different field of illumination for the illuminating light than the field of view of the detector measuring the emitted fluorescence, which is a serious disadvantage, as will further become apparent.

The term "field of view" for an optical detector as used herein refers to the region within a sample which is observable by the detector. The term "field of illumination" for an illuminating light is defined herein as the region within a sample which is illuminated by the excitation light.

Another system uses a bifurcated fiber optic bundle for this purpose. (Science, Vol. 217, Aug. 6, 1982, Intracellular Oxidation-Reduction State Measured in situ by a Multichannel Fiber-Optic Surface Fluorometer, Avraham Mayevsky and Britton Chance, pp. 537–540). Here too inefficiencies in the fiber optics require the use of a light source and detector unsuitable for incorporation into a probe of practical size. These inefficiencies relate to the loss of UV and visible light during transmission through the fibers and a disadvantageous difference between the field of illumination established by the fibers transmitting the illuminating light and the field of view of the detector established by the fibers transmitting the emitted fluorescence. This becomes especially significant in highly light absorbent samples where the penetration of light into the sample is limited to a very short distance.

Although this invention can be used with a wide range of materials, it is principally intended for the real-time determination by their fluorescence of the characteristics of living biological materials directly in process. The application of fluorescence measurements in biological systems is well known in the art. (Fluorescence Assay in Biology and Medicine, Volume 1, Sidney Undenfriend, 1962, pp. IX–XII). For example, living cells emit visible fluorescent light at 460 nm when illuminated with ultraviolet light at 340 nm. Most of this fluorescence is due to the intracellular accumulations of the reduced forms of nicotinamide adenine dinucleotide and nicotinamide adenine dinucleotide phosphate, (NAD(P)H), important energy storage molecules common to living matter. This principle has been used to study metabolism in intact tissues including brain, liver, kidney, and testis tissue. (U.S. Pat. No. 3,313,290, Britton Chance and Victor A. Legallais and Science, Vol. 217, Aug. 6, 1982, Intracellular Oxidation-Reduction State Measured in Situ by a Multichannel Fiber-Optic Fluorometer, Avraham Mayevsky and Britton Chance, pp 537–540). Suspensions of yeast, bacteria and fungi have also been studied with the aid of fluorescence. (Applied and Environmental Microbiology, Estimation of Fermentation Biomass Concentration by Measuring Culture Fluorescence, Feb. 1978, pp. 337–343, D. W. Zabriskie and A. E. Humphrey).

OBJECTS OF THE INVENTION

It is therefore the object of the present invention to provide a new probe and method for measuring the characteristics of materials by their fluorescence in applications where:

1. Rapid measurement response times are required so that the measurement is made on-line or in real time with respect to process.
2. High measurement sensitivity is needed to quantitate low levels of fluorescence.
3. Long term instrument stability must be high, making periodic instrument recalibrations unnecessary.
4. An in-place measurement is used to avoid the problems associated with sampling such as the logistics of obtaining the sample, process homogeneity, risks of disturbing the process, or sample stabilization prior to measurement.
5. The portion of the probe which is inserted into a process vessel, such as a fermentor, must be capable of in-situ sterilization with steam at 250° F. during the sterilization of the vessel.
6. The probe is to be inserted through a process vessel wall using standard industrial nozzles, such as an "INGOLD" fitting.
7. The probe may be inserted to a depth sufficient to insure an adequate level of mixing in agitated process vessels.

Examples of materials include liquid solutions, surfaces of solids, mixtures of gases and suspensions of solids where at least one component is fluorescent (i.e. a fluorophore). Alternatively, this invention can be used with non-fluorescent compounds of interest if these compounds can be selectively coupled with a fluorescent dye. Components of interest may be chemical reactants, reaction intermediates, products, by-products, impurities, or inerts within a system. This instrument is especially suited for use in biological reactors such as fermentors which require that a probe operate within a sterile or aseptic environment.

SUMMARY OF THE INVENTION

In accordance with the present invention the optical apparatus for measuring the characteristics of materials by their fluorescence employs an excitation beam source immersed in a circular concave mirror which collects and redirects the excitation beam into a convergent beam. The beam having a predetermined field of illumination illuminates the process sample. The beam is preferably projected all the way into the sample until it is completely absorbed. Process material fluorescence formed in the aforementioned field of illumination passes back through the same window through which the excitation beam passed and is measured by a fluorescence photo detector.

It is important for the purposes of the present invention that the field of view of the fluorescence photo detector substantially encompass the field of illumination of the excitation beam, such that the fluorescence emitted in the field of illumination is substantially within the field of view of the detector.

In a preferred form of the invention the light source is a stabilized ultraviolet lamp, and its beam passes through a band pass filter at the beam focal point, and then diverges to illuminate the process sample through a quartz window located at the probe end. Also preferably the process material fluorescence passes through a multielement high pass filter and impinges on a fluorescence photo detector located adjacent to and surrounding the focal point of the excitation beam forming a coaxial optical system. Preferably the eectrical signal produced at the fluorescence photo detector is coupled to a low noise amplifier located in a sealed chamber at the back end of the probe and the amplifier fluorescence signal is then conveyed via cable to the power supply, display and control section of the apparatus.

In the power supply, display, and control section of a preferred form of the apparatus the fluorescence signal is further processed for gain, trim, and offset. The trimmed fluorescence signal is then applied to a digital volt meter for display, and to a strip chart recorder to produce a permanent record of the process material fluorescence to indicate trends. Alarm comparators with relay contact outputs are also provided for automatic process control applications.

Likewise, in a preferred form of the apparatus, an additional photo detector is located on the output side of the low UV band pass filter, adjacent to the UV excitation beam. This photo detector is illuminated by the off axis portion of the filtered excitation beam. The electrical signal produced at the excitation photo detector is coupled to a low noise preamplifier located in a sealed chamber at the back end of the probe. The amplified excitation signal is then conveyed via cables to the power supply, display and control section of the apparatus. In the power supply display and control section of the apparatus the amplified excitation signal is compared with a fixed reference voltage. The error signal produced at the comparator is used to control the output of the lamp regulator. The output of the lamp regulator is conveyed to the probe section of the apparatus. At the probe section of the apparatus the output of the UV lamp regulator is conveyed by wires to the lamp immersed in the condensing mirror. The feedback loop described stabilizes the UV lamp based on light output. Likewise, the lamp feedback system stabilizes the excitation beam illuminating the process material. More particularly the lamp feedback loop stabilizes the characteristic fluorescence produced in the process material from changes and drifts associated with changes and drifts in the excitation beam produced at the lamp. This results in a very stable apparatus with good repeatability, and immunity to outside influences such as line voltage variations, room temperature changes or UV lamp aging.

As used herein, the term "fluorescence photo detector" is to be given a broad scope as to include devices whose electrical output varies with applied light; this includes photo diodes, photo resistors, optical thermocouples, etc. Likewise the term "lamp" is to be given a broad scope as to include devices whose light output varies with applied electrical input; this includes mercury arc lamps, fluorescent lamps, Nernst glowers, lasers, etc. Likewise, the term "seal" broadly includes devices intended to prevent leakage: this includes "O" rings, compression seals, line contact seals, frit seals, etc. Likewise, the term "filter" broadly includes devices selecting certain wavelengths while rejecting others without refracting the light at the selected wavelength; this includes colored filter glasses, organic dye filters, thin film multiple reflection interference filters, etc. Likewise the term "mirror" is to be given a broad scope as to include devices intended to collect and converge or diverge light; this includes lenses, prisms, brewster angle reflectors, fiber optic bundles, etc. Likewise the term "window" is to be given a broad scope to include flat surfaces or curved surfaces to aid in the collection of dispersed fluorescent light. Likewise, the term "vessel" is to be given a broad scope to include any device used to contain the sample including cuvettes, beakers, flasks, petri plates, tanks, pipes, etc.

DETAILED DESCRIPTION OF THE INVENTION

The present invention is directed to an improved optical apparatus and method for measuring fluorescence in real time. The design employs a new measurement principle wherein the field of illumination of the illuminative light is substantially contained within the field of view of the detector measuring the emitted fluorescence. In a preferred form, the path followed by the illuminating light to the sample and the path followed by the emitted fluorescence to the detector are essentially coaxial in the overall sense. This principle makes efficient use of the exciting light and makes the measurement sensitive to low concentrations of fluorophores since the field of view of the detector completely encompasses the fluorescence emitted within the field of illumination of the lamp. This is not the case in some prior art instruments where a substantial angle exists between lamp and detector paths. Since the principle is a special case of a surface detector, the measurement is more sensitive to highly light absorbant samples than procedures which measure fluorescence through a surface different than the surface used for illumination.

This principle permits the sensor to be assembled as a compact cylindrical probe which can be directly inserted in a process vessel through a variety of standard nozzles. The cylindrical geometry of the probe facilitates the sealing of the probe to protect it externally from water (e.g. from tank washing, foam overs, accidental spills) or to allow the probe to contain a dry gas (e.g. to avoid water condensation within the probe). This configuration avoids many of the problems normally associated with providing stable and representative samples in real time to prior art instruments which employ sample chambers. The avoidance of a sample chamber also permits the optical path length to vary as a function of the light absorbing species in the sample as defined by total absorption. This enhances the range and sensitivity of the probe over that obtainable at a single fixed path length. Light losses due to reflectance from the probe window are minimized by arranging the measurement plane established by the window to be normal to the optical path in the overall sense. The probe may be inserted into the vessel to a suitable distance away from the vessel wall where a satisfactory level of mixing is achieved in agitated tanks. A sensor is incorporated in the probe for measuring the intensity of the excitation wavelength which is used to regulate the power supplied to the illuminating lamp to stabilize its output. This sensor is also used to detect failure of the lamp. The probe is designed so that the portion of the probe inserted into a process vessel may be sterilized in-situ with steam and to operate aseptically in the process after sterilization. The probe is designed to work with any combination of excitation and fluorescent wavelengths through the selection of the filters installed in the probe. The probe is suitable for monitoring or process control applications. The probe may also be used in applications which do not require vessels such as measuring the fluorescence of surfaces, intact tissues, organs, or open bodies of liquid, etc.

For the purpose of illustrating the invention, there is shown in the drawings a form which is preferred; it being understood, however, that this invention is not limited to the precise arrangements and instrumentalities shown.

Figure 1:
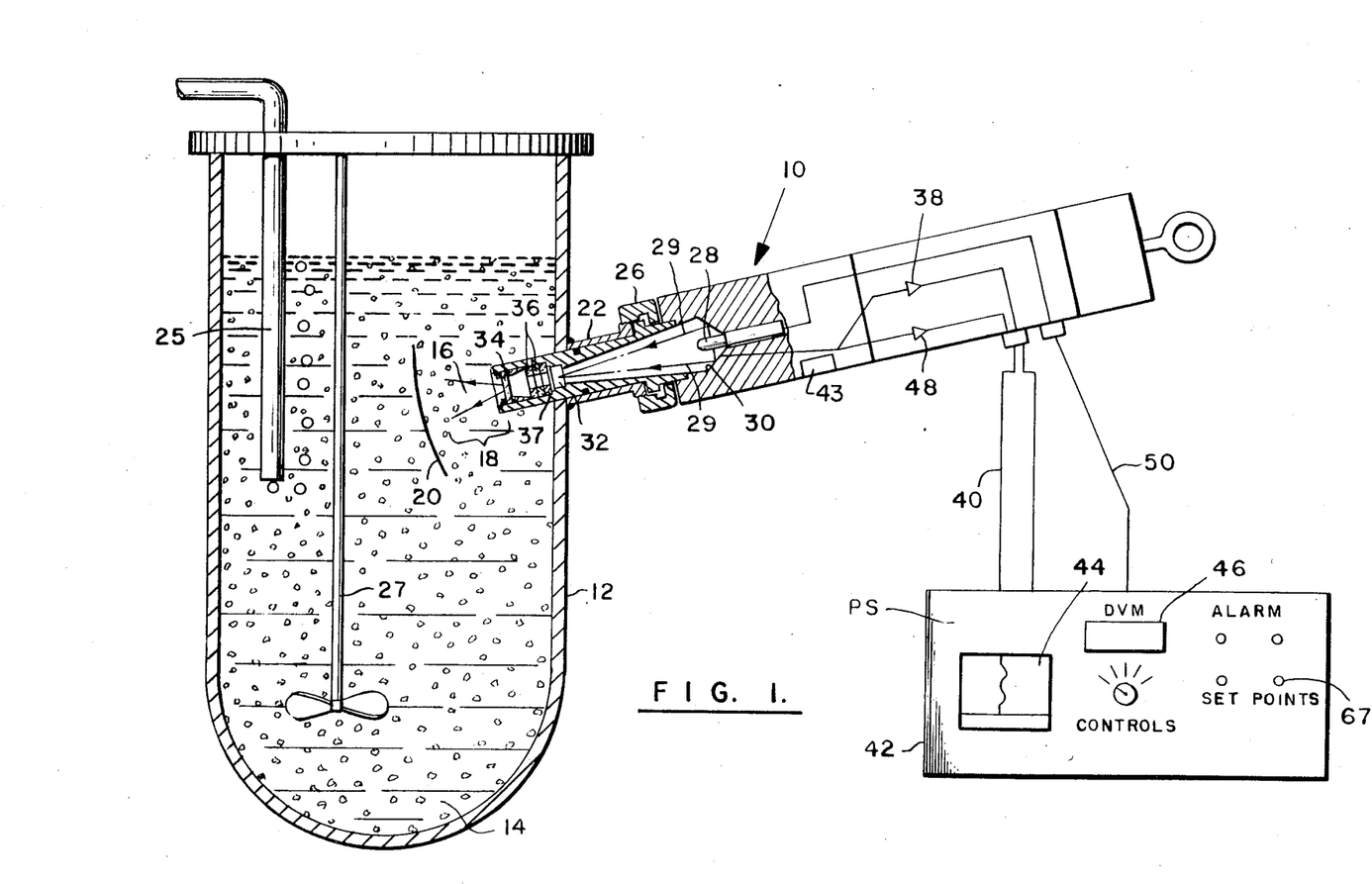
FIG. 1 is a longitudinal view of the apparatus partially in section.

Referring to the drawings in detail, wherein like numerals indicate like elements, there is shown in FIG. 1 an optical probe apparatus of circular cross-section designated in general by the numeral (10) for measurement of the characteristics of a biological material by measuring the characteristic fluorescence of the biological material when the material is illuminated by a beam exiting the probe end. As an exemplary embodiment the apparatus (10) is shown mounted in and projecting into a fermentor (12) containing a suspension of microorganisms (14) in various stages of biological growth. The excitation beam (16) is shown probing into the biological material along the biological absorption gradient (18) to a distance (20) at which the excitation beam is totally absorbed. This distance varies with biological concentration at any given time. The probe is mounted in an "INGOLD" fitting (22) which is welded to the fermentor (12) and is sealed to this fitting with an O-ring (24). The ring nut (26) holds the probe securely in the "INGOLD" fitting (22). The tank (12) is provided with a stirring mechanism (27), and tubing (25) providing air, nutrient and pH adjustment.

The growth of the biological population (14) in vessel (12) is monitored by the optical probe (optrobe) apparatus (10). Such apparatus, described in more detail hereinafter, employs a lamp (28) immersed in a circular condensing mirror (30). The light reflects off the condensing mirror to form a converging beam with a focal point located at the filter (32). Filter (32) is not a lens and does not appreciably refract the beam or change its path. Its function is to permit passage of a beam of a preselected wavelength. The diverging beam of filtered light passes through the probe window (34), preferably made of quartz, and illuminates the biological material (14) contained in the beam (16) along the biological absorption gradient (18). Preferably the beam is projected into the biological material (14) until total absorption occurs, as schematically illustrated at the total absorption plane (20). It is understood that plane (20) is not a geometrical plane but rather a surface along which total absorption occurs. As the cell population (14) increases, more and more fluorescence is produced in the excitation beam (16). This fluorescence passes back through the probe window (34) and filters (36) and is sensed by the return fluorescence photo detector (37). Filters (36) are not a lens and do not appreciably refract the beam or change its path. The signal is amplified by the fluorescence photo amplifier (38) and conveyed via the signal cable (40) to the power supply (PS), display and control section (42) of the apparatus. The fluorescence signal is displayed on a digital volt meter (DVM) (46) and recorded on the fluorescence recorder (44). The fluorescence signal is also compared with setpoints (67) for use in automatic process control applications. The lamp photo detector preamplifier (48) is used as part of the lamp output control feedback loop and is conveyed via cable (40) to the PS display and control section (42) of the apparatus. This servo loop is explained in greater detail hereinafter with reference particularly to FIG. 5. Power for the lamp (28) originates in the PS display and control section (42) of the apparatus and is conveyed via cable (50) to the probe (10) and lamp (28).

Figures 2, 9, 10, 11:
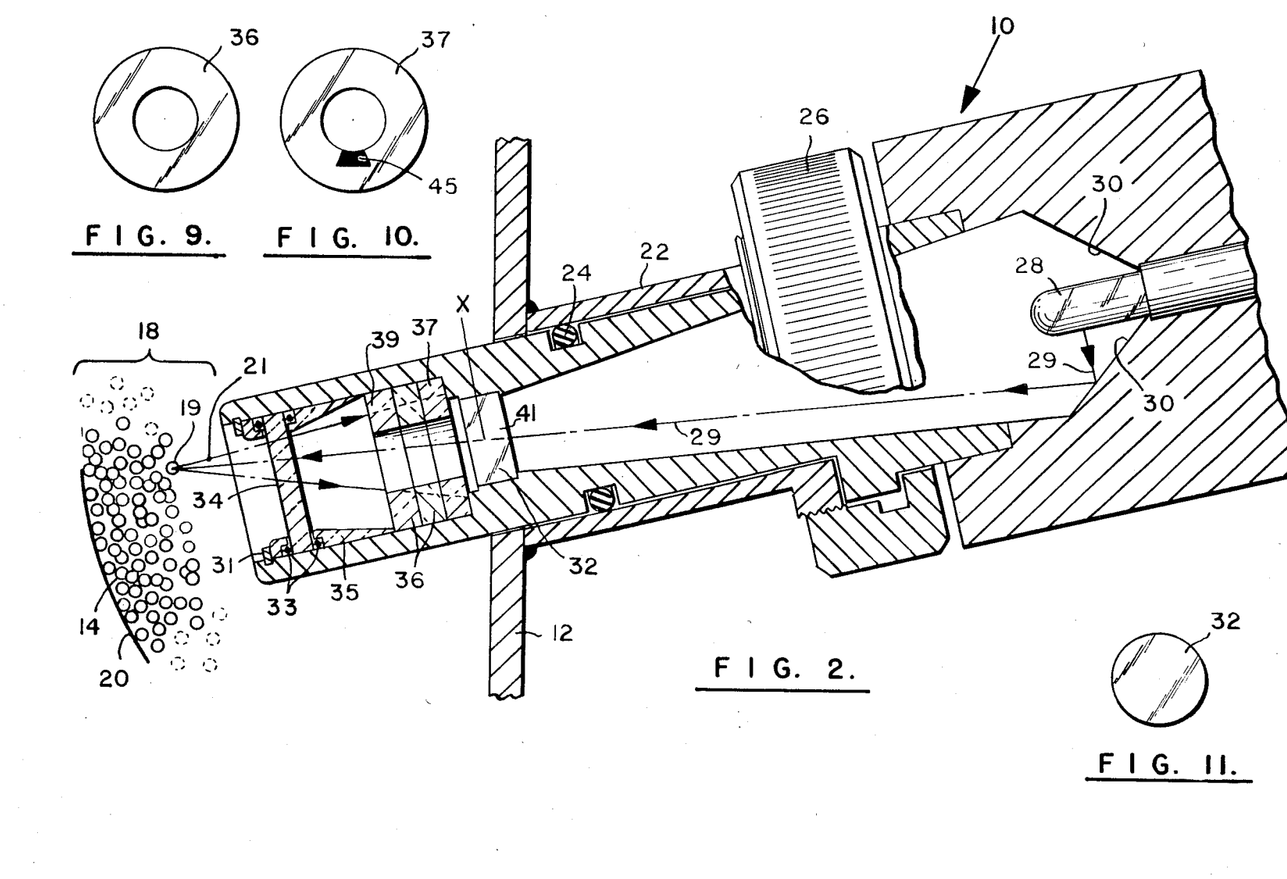
FIG. 2 is a transverse partial sectional view illustrating the probe optics and overall construction.
FIGS. 9, 10 and 11 are front views of items 36, 37 and 32, respectively, which appear in FIG. 2.
Figure 3:
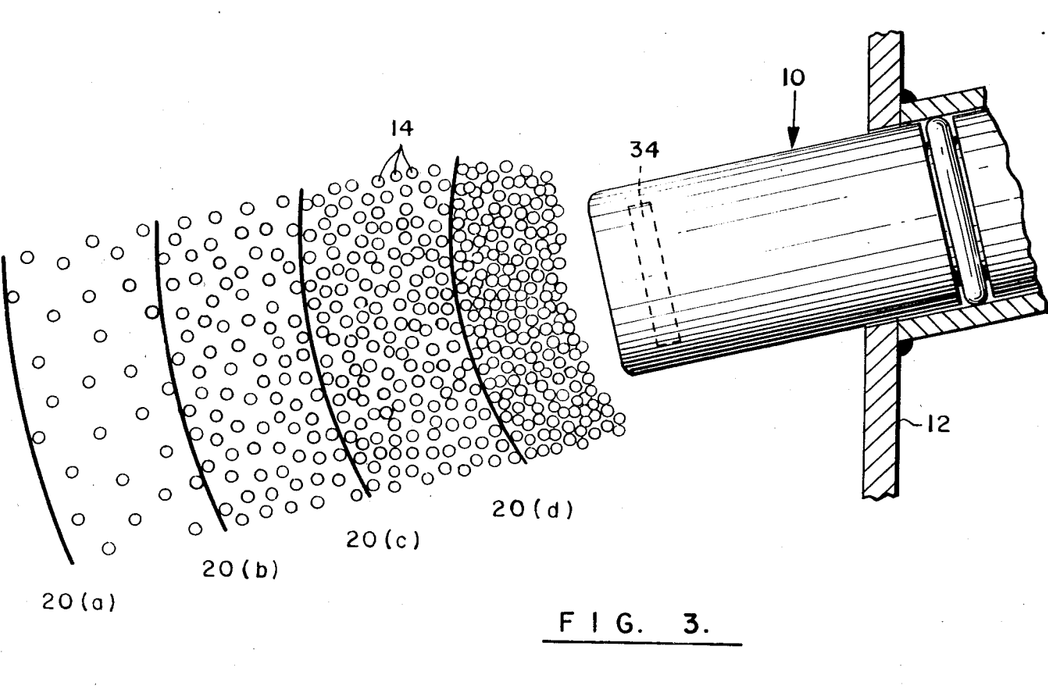
FIG. 3 is a schematic view of a probe and a measured medium, illustrating total absorbance in accordance with this invention.

Referring to FIG. 2, there is shown a transverse sectional view illustrating the probe (10) optics and overall construction in more detail. Light produced at lamp (28) is collected by a concave circular mirror (30) and is redirected by reflection to converge to a focal point (X) located at the center of the bandpass filter (32) (300 to 400 nm for example for NAD(P)H). The beam passes through the bandpass filter (32) (see also FIG. 11) and diverges through openings within elements (36), and (37) (see also FIGS. 9 and 10), to fully illuminate the probe window (34) and the biological material (14) beyond. Rays 29 of the beam continue along their paths in the biological absorption gradient (18) until it is absorbed at some point such as (19); total absorption of all rays occurs within the distance defined by total absorption plane (20). It is also understood that the location of the total absorption plane (20) is a function of cell concentration of biological material (14) present at the time of measurement. As the cell concentration increases the plane of total absorption (20) will move closer to the probe (10) and window (34), as indicated by the total absorption planes (20)$a$, (20)$b$, (20)$c$ and (20)$d$ in FIG. 3. An increase of cell population or other ingredients draws the total absorption limit closer to the window but does not alter the solid angles which delimit the field of illumination (FI) and the field of view (FV) of the fluorescence photo detector (37). The fluorescence photons (21), pass back through the window (34), reflect off the fluorescence condensing mirror (35) and are redirected by reflection to the fluorescence highpass filters (36) (400–600 nm for example for NAD(P)H) and the fluorescence photo detector (37).

The fluorescence photo detector (37) converts these photons (21) to an electrical signal which is conveyed via wire to preamplifier (38) (FIG. 1) for amplification. For clarity only some rays (29) and (21) are shown, however, other paths do occur. As shown in FIGS. 9–11, the bandpass filter (32) and the return highpass filters (36) and photo detector (37) are shown in detail and rotated 90° to front view for clarity. Thus shown, item (32) is circular and items (36) and (37) are annulus shaped. The exciting beam shown as ray (29) in FIG. 2 passes through filter (32) and then through the holes in the return fluorescence highpass filters (36) and the fluorescence photo detector (37).

Additional construction details of the apparatus of FIG. 2 include window seal "O" rings (33) to preclude leakage of process material liquid (14) from entering the interior of the probe. An "O" ring retainer (31) is provided for probe disassembly. "O" ring seal (24) is provided to form a seal with the "INGOLD" fitting (22) to preclude process material (14) leaking beyond this point. Nut (26) is employed to secure the probe (10) to the fitting (22).

In combination with the fluorescence photo detector (37) and integrated with it is an additional photo detector (45) (FIG. 10), employed to control the lamp (28) output. This photo detector is the sensing device in the lamp control servo loop and is described in greater detail in reference to FIG. 5. The output of the lamp photo detector is conveyed via wire to the lamp output photo detector amplifier (48) for amplification.

Figure 4:
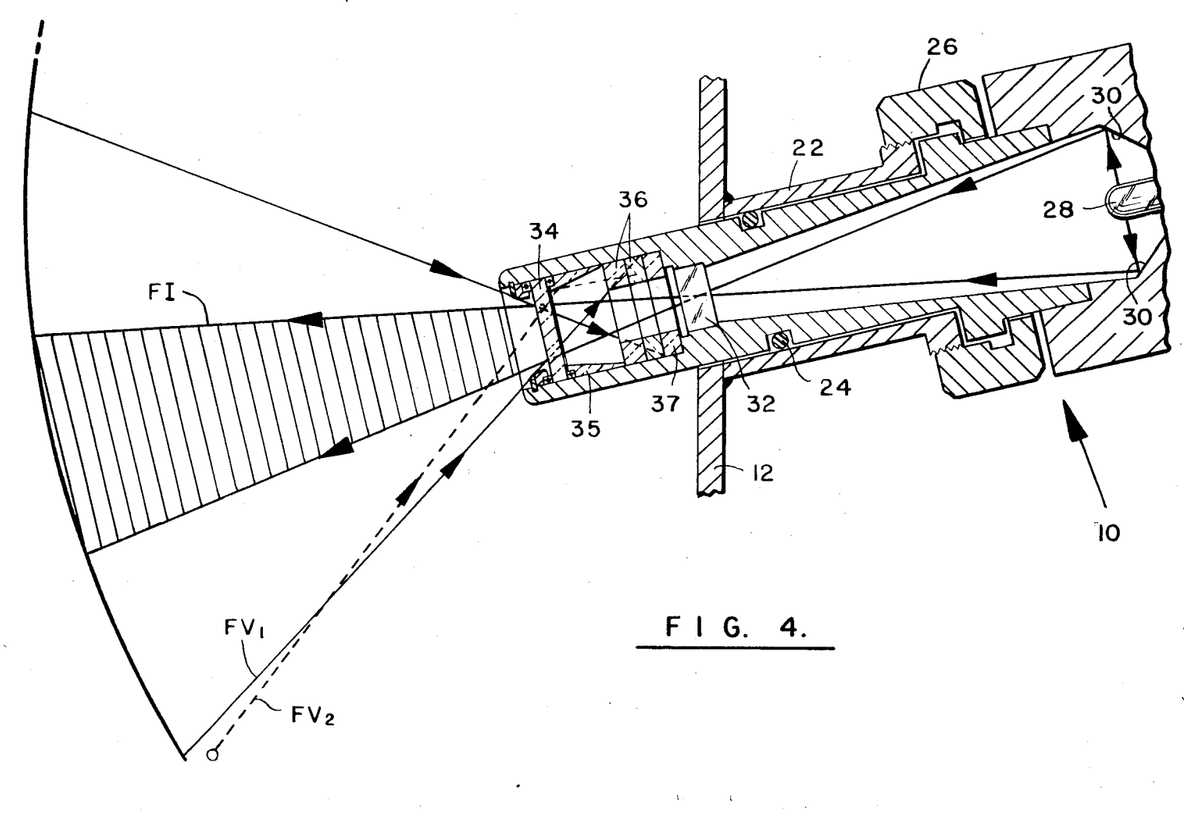
FIG. 4 is a schematic view of a probe, illustrating the field of illumination and field of view in accordance with this invention.

Referring to FIG. 4, there is shown the end of the probe (10). Both the field of illumination (FI) of the lamp and the field of view (FV) of the photo detector (37) are shown. The direct field of view (FV$_1$) as well as the reflected field of view (FV$_2$) of the photo detector (37) are shown. The field of view (FV$_1$ or FV$_2$, but both hereinafter referred to simply as 'FV') of the photo detector (37) is broader than, and totally encompasses, the field of illumination (FI) of the lamp. This is accomplished by making the distance between the photo detector (37) and the window (34) less than the distance between the window (34) and the lamp. It is important for purposes of obtaining accurate fluorescence measurements, that the field of view (FV) substantially, and preferably wholly, encompasses the field of illumination (FI). Otherwise, as occurs in the many of the prior art devices, a portion of the fluorescence is not detected by the photo detector and only a low sensitivity is obtained.

Figure 5:
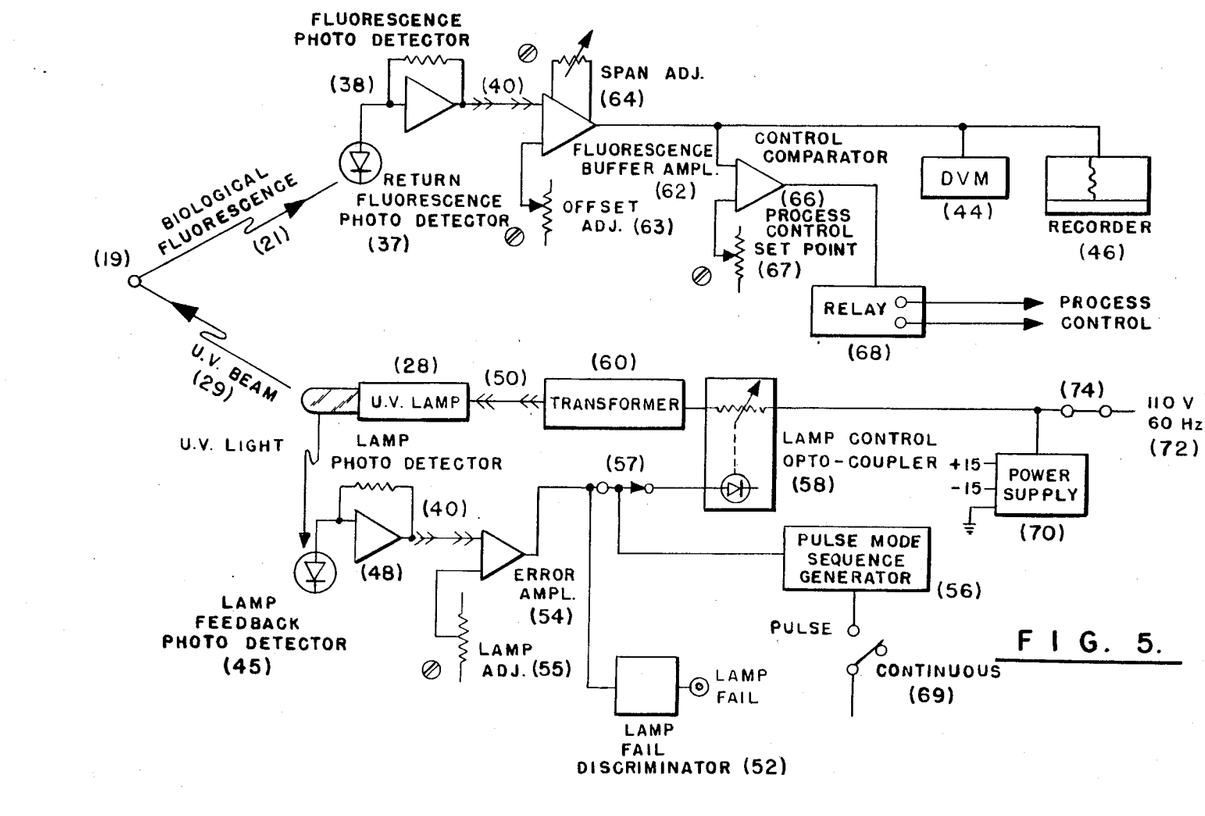
FIG. 5 is a block diagram of the fluorescence measurement system electronics and the lamp intensity control servo system electronics.

Referring to FIG. 5, there is shown a block diagram of one form of the fluorescence measurement system electronics and the lamp intensity control servo system electronics selected for illustration in the drawings. Beginning with 110 volt mains applied (72) power, switch (74) conveys the power to the low voltage supply (70) and to the lamp control opto coupler (58) which is the control element for transformer (60), and via cable (50) for lamp (28). The lamp feedback photo detector (45) senses the lamp intensity and conveys this signal to the error amplifier (54) via the lamp photo detector amplifier (48) and cable (40). The error amplifier (54) compares the lamp intensity signal from cable (40) with a reference signal developed at the lamp intensity adjust potentiometer (55). Intensity variation error signals produced at the error amplifier (54) directly control the lamp control opto coupler (58), producing stable lamp (28) output. A lamp fail discriminator circuit and indicator (52) monitors the error signal from error amplifier (54) and determines proper lamp operation. The pulse mode sequence generator (56) controls the lamp output via switch (57) and permits flashed operation of the lamp (28). Continuous or pulse operation is selected as switch (69).

Biological fluorescence (21) produced at location (19) in the medium being tested is converted to an electrical signal at the return fluorescence photo detector (37). This signal is conveyed to the fluorescence buffer amplifier (62), via the fluorescence photo detector amplifier (38) and cable (40). The fluorescence buffer amplifier (62) trims the fluorescence signal for span and offset via the span adjustment potentiometer (64) and the offset adjustment potentiometer (63). The fluorescence signal is displayed on digital voltmeter (44) and recorded on recorder (46). The control comparator (66) compares the trimmed fluorescence signal from the fluorescence buffer amplifier (62) with a setpoint voltage developed at the process control setpoint potentiometer (67). The output of the control comparator actuates relay (68). Relay (68) is the control element used in automatic process control applications.

Filters (32) and (36) are not always required for fluorescence measurements. Should the intrinsic wavelengths produced by the illuminating source be limited to the wavelengths of interest for excitation, then filter (32) may be omitted. This could occur, for example, if the light source were a laser. Should the intrinsic sensitivity of the detector be limited to the wavelengths of the emitted fluorescence, then filter (36) may be omitted.

It may be advantageous in certain situations to operate the probe in a pulse mode. Further defined, this involves modifications to the power supply display and control section of the apparatus. This modification enables the excitation lamp to be flashed at a controlled rate and duration with the resultant return biological fluorescence determined by the return fluorescence photo detector and optics during the lamp off period. Applications and advantages of this modification include reduction of nonfluorescent material back scatter, reduction of light induced damage to UV sensitive organisms, and lengthening of the useable lamp life.

The apparatus described in this invention includes provisions for operation in the pulse mode. Provisions are also incorporated in the probe optics to include polarizers (39), (41) adjacent filter (32) and the return fluorescence measurement filter (36). Polarized light improves the measurement characteristics of materials in some cases.

In situations where the probe will be exposed to temperature extremes such as those encountered in outdoor applications, it may be advantageous to incorporate a heater (43) within the probe to regulate its temperature within acceptable limits.

The probe may be used in connection with other accessories designed for specific analytical functions. These include attaching a chamber containing a fluorescent gas to the probe for the purpose of measuring the temperature of the environment surrounding the chamber by the intensity of the fluorescence emitted by the gas since the intensity is often temperature dependent. Other chambers useful as accessories in some cases include a semi-permeable membrane permeable to the compound to be analyzed but impermeable to other substances supplied to the chamber. The function of the substances within the chamber is in some cases to enhance the fluorescence of weak fluorophores to fluoresce in response to concentrations of non-fluorescent diffusible compounds such as $O_2$, $H^+$, etc.

The probe may also be used without filters (32) and (36), or may be equipped with identical filters. In this case the instrument will measure the amount of light reflected by particulates in the sample. In this mode the instrument becomes a reflectometer or nephrometer.

The following Examples are illustrative of the invention. They are not intended to limit the scope of the invention, which is defined in the appended claims.

EXAMPLE 1

Figure 6:
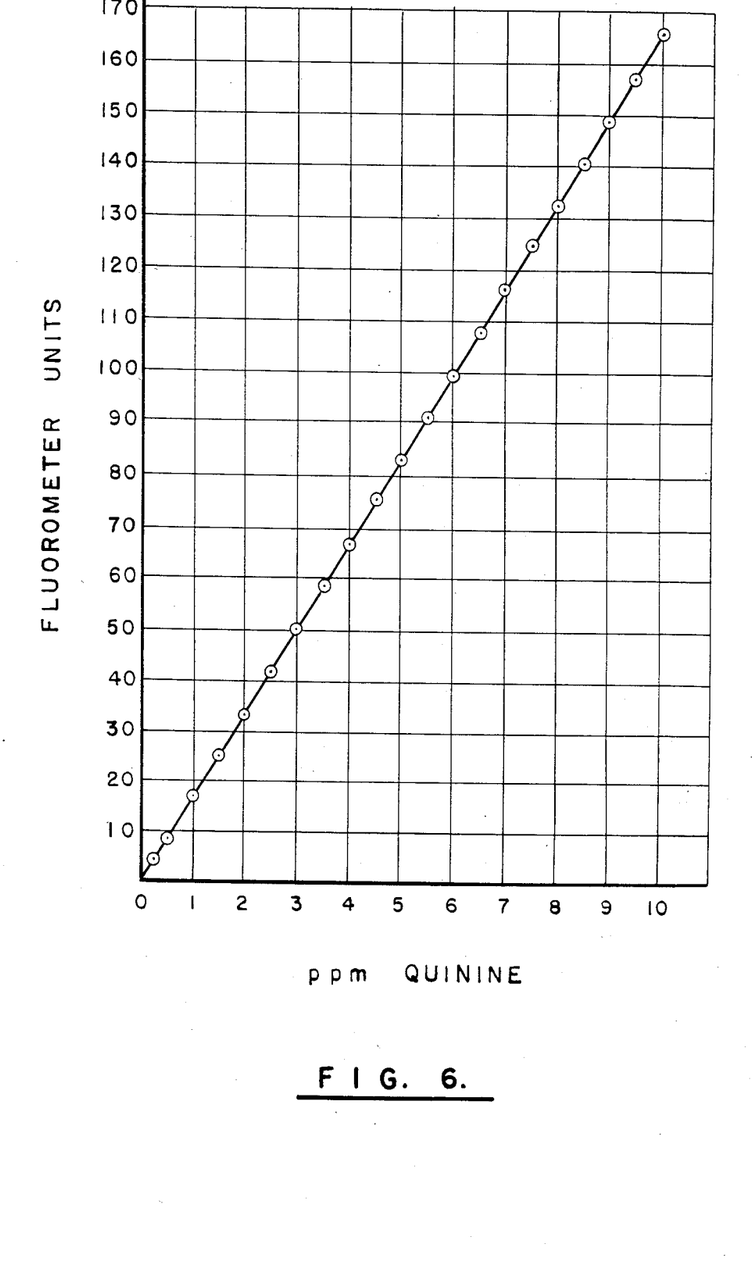
FIGS. 6, 7 and 8 are instrument response plots in accordance with actual runs as reported in Examples 1, 2 and 3 respectively.

A process vessel was filled with water containing 50 mmole/l of $H_2SO_4$. The solution was stirred gently and the temperature controlled at 30° C. To this vessel was added aliquots of a 1000 ppm solution of quinine in 50 mmole/l of $H_2SO_4$. Quinine is a fluorophore having an excitation maximum at 340 nm and a fluorescent emission maximum at 460 nm under these conditions. The instrument response in fluorescence units at a gain of 100 is plotted in FIG. 6 as a function of quinine concentrations in the range of 0-10 ppm.

EXAMPLE 2

Figure 7:
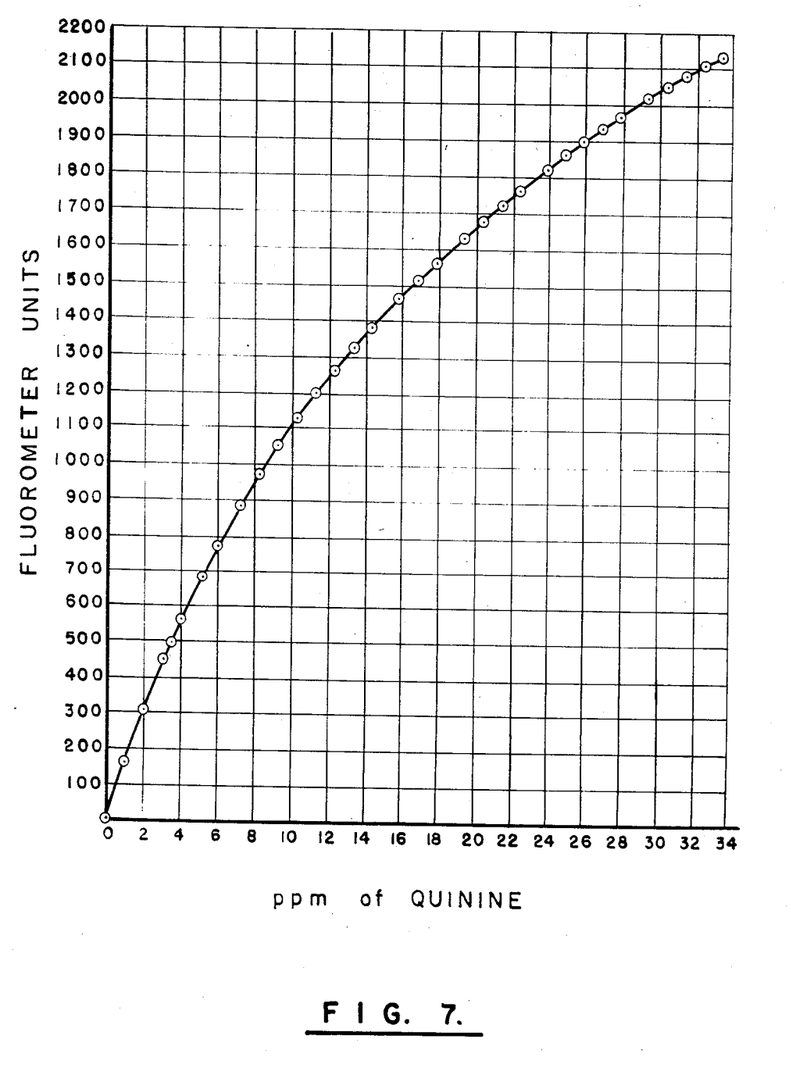

The run of Example 1 was repeated to give quinine concentrations in the range of 0-34 ppm. The results are shown in FIG. 7.

EXAMPLE 3

Figure 8:
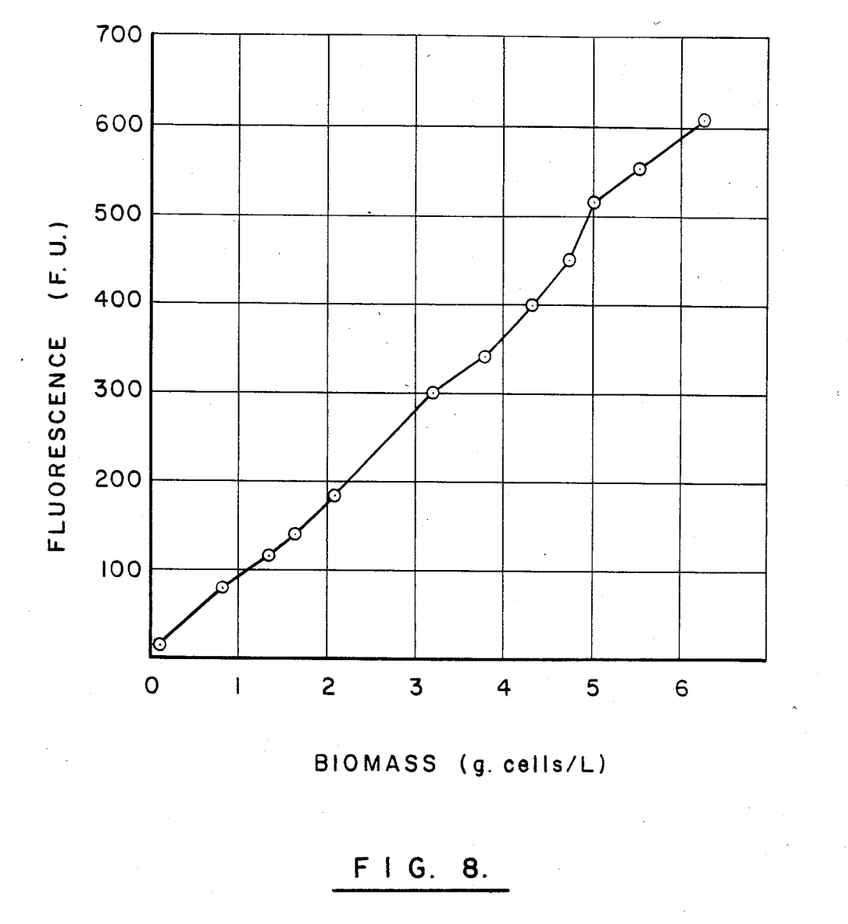

A fermentor was used to produce *Corynebacterium callunae* using procedures generally known to the art. Initially the fermentor contained 0.1 g/l of bacteria. At the end of the process, the fermentor contained 6.3 g/l. The fluorescence of the culture was recorded during the process. FIG. 8 shows the correlation of the fluorescence of the culture with the concentration of bacteria in g/l.

We claim:

1. Apparatus for measuring in real time the energy level of a liquid biological medium contained in a biological reactor, the medium containing living cells, by measuring fluorescence emitted by the cells, comprising means for projecting a directed symmetrical diverging illuminating beam of ultraviolet light along a path into the cells, and photosensitive means for detecting emitted fluorescence from within the cells, wherein the field of illumination of the illuminating beam is encompassed by the field of view of the photosensitive means detecting the emitted fluorescence and wherein at least a portion of the apparatus extends into the reactor.

2. In a method for measuring in real time the energy level of a liquid biological medium contained in a biological reactor, the medium including living cells, by measuring fluorescence emitted by the cells, the steps which comprise projecting a directed symmetrical diverging illuminating beam of ultraviolet light along a path within a field of illumination into the cells being tested, and detecting within a field of view fluorescence emitted from the cells, the field of illumination of the illuminating beam being encompassed by the detecting field of view.

* * * * *